United States Patent [19]
Wong-Madden et al.

[11] Patent Number: 5,763,244
[45] Date of Patent: Jun. 9, 1998

[54] METHOD FOR CLONING AND EXPRESSION OF PHOSPHORYLATION-DEPENDENT PROTEIN KINASE

[75] Inventors: Sharon T. Wong-Madden, Newburyport; Richard J. Roberts, Wenham, both of Mass.

[73] Assignee: New England Biolabs, Inc., Beverly, Mass.

[21] Appl. No.: 520,928

[22] Filed: Aug. 30, 1995

[51] Int. Cl.$^6$ .............................. C12N 15/54; C12N 9/12
[52] U.S. Cl. .............................. 435/172.3; 435/195
[58] Field of Search ........................ 435/172.2, 172.3, 435/194

[56] References Cited

PUBLICATIONS

Her, et al., Nucleic Acids Research, 19:3743 (1991).
GenBank Accession No. X58712 (1993).
Wu, et al., Mol. Cell Biol., 13:4539 (1993).
GenBank Accession No. L14936 (1993).
Fabian, et al., Mol. Cell Biol., 13:7170 (1993).
Mansour, et al., Science, 265:966 (1994).
Marshall, Cell, 80:179 (1995).
Yan, et al., Nature, 372:798 (1994).
Burgering, Nature, 376:599 (1995).
Huang and Erikson, Proc. Natl. Acad. Sci., USA 91:8960–8963 (1994).
Pages, et al., EMBO J., 13:3003–3010 (1994).
Kunkel, et al., Meth. Enzymology, 154:367–382 (1987).
Solomon, et al., Mol. Biol., Cell., 3:13–27 (1992).
Fesquet, et al., EMBO J., 12:3111–3121 (1993).
Poon, et al., EMBO J., 12:3123–3132 (1993).
Solomon, et al., EMBO J., 12:3133–3142 (1993).
Riggs, In Current Protocols in Molecular Biology (Ausubel, et al., eds.) Greene Publishing and Wiley–Interscience, NY (1992), 16.6.1–16.6.14.
Potts, et al., J. Biol. Chem., 238:2593–2594 (1963).
Schmidt and Skerra, Protein Engineering, 6:109–122 (1993).
Smith, et al., J. Biol. Chem., 263:7211–7215 (1988).
Bao, et al., Gene, 109:167–168 (1991).
Luckow, et al., J. Virol., 67:4566–4579 (1993).
Winans, et al., J. Bacteriol., 161:1219–1221 (1985).
Russell, et al., J. Bacteriol., 171:2609–2613 (1989).
Ferenci and Klotz, FEBS Letters, 94:213–217 (1978).
Kyriakis, et al., Nature, 369:156 (1994).
Sale, et al., The EMBO Journal 14(4):674–684 (19950.
Zheng, C. F., et. al. (1993) J. Biol. Chem. 268 (32), 23933–23939.

*Primary Examiner*—Charles L. Patterson, Jr.
*Attorney, Agent, or Firm*—Gregory D. Williams

[57] ABSTRACT

The present invention relates to a method for cloning and expressing an exogenous phosphorylation-dependent protein kinase in *E. coli,* and in particular to the co-expression of one or more components of a signal-transduction pathway in *E. coli.*

31 Claims, 6 Drawing Sheets

SEQ1 ←—  
GCTCCCGCGGAGGCTCCGGATGGACCAC  
StuI

SEQ2 —→  
AAGCGGCTGGAGGCCTTCCTTACCCAG  
StuI

Inverse PCR  
StuI Digestion  
Ligate

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: unknown ( i i ) MOLECULE TYPE: synthetic oligonucleotide ( x i ) SEQUENCE DESCRIPTION: SEQ ID NO:1:

CACCAGGTAG GCCTCGGAGG CGCCCTCG                       2 8

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: unknown ( i i ) MOLECULE TYPE: synthetic oligonucleotide ( x i ) SEQUENCE DESCRIPTION: SEQ ID NO:2:

AAGCCGGCTG GAGGCCTTCC TTACCCAG                       2 8

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: synthetic oligonucleotide ( x i ) SEQUENCE DESCRIPTION: SEQ ID NO:3:

AGAGCCCTGA TGCTAGCCCG GAGG                            2 4

( 2 ) INFORMATION FOR SEQ ID NO:4:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: unknown ( i i ) MOLECULE TYPE: synthetic oligonucleotide ( x i ) SEQUENCE DESCRIPTION: SEQ ID NO:4:

TTGCGAATTC TGTTACACTG CAGTACG    27

( 2 ) INFORMATION FOR SEQ ID NO:5:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: unknown ( i i ) MOLECULE TYPE: synthetic oligonucleotide ( x i ) SEQUENCE DESCRIPTION: SEQ ID NO:5:

TTTTTCGCGA AGGAAAGAGA TGCTGGG    27

( 2 ) INFORMATION FOR SEQ ID NO:6:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: unknown ( i i ) MOLECULE TYPE: synthetic oligonucleotide ( x i ) SEQUENCE DESCRIPTION: SEQ ID NO:6:

TTTTTCGCGA TATCGTCCAC AAGCTGTCCA CT    32

( 2 ) INFORMATION FOR SEQ ID NO:7:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: unknown ( i i ) MOLECULE TYPE: synthetic oligonucleotide ( x i ) SEQUENCE DESCRIPTION: SEQ ID NO:7:

TTTTTGCGCA GCTCCGAGCC CGAGC    25

( 2 ) INFORMATION FOR SEQ ID NO:8:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: unknown ( i i ) MOLECULE TYPE: synthetic oligonucleotide ( x i ) SEQUENCE DESCRIPTION: SEQ ID NO:8:

TTTTGGATCC GTATCAGTCG ACATACAT    28

METHOD FOR CLONING AND EXPRESSION OF PHOSPHORYLATION-DEPENDENT PROTEIN KINASE

FIELD OF THE INVENTION

The present invention relates to a method for cloning and expressing an exogenous phosphorylation-dependent protein kinase in *E. coli*, and in particular to the co-expression of one or more components of a signal-transduction pathway in *E. coli*.

BACKGROUND OF THE INVENTION

All living cells need to adapt to the conditions in which they find themselves growing. For instance, they may need to adjust their metabolism from one food source to another when nutrients are scarce. This usually involves a change in gene expression so that new enzymes suited to the new food source are produced. In other situations cells might need to respond to signals telling them whether or not to divide. In eukaryotes, research over the last ten years has identified a number of pathways by which signals are transduced from the outside of the cell to the nucleus. These so-called signal transduction pathways are most often mediated by protein kinases (an example is shown in FIG. 1).

Typically, a receptor molecule located in the outer cell membrane binds a particular small molecule, such as a hormone, that is present outside of the cell. In response the receptor undergoes a conformational change that activates it to function, for example, as a protein kinase. This protein kinase will then phosphorylate another component of its signal transduction pathway, possibly an inactive form of a protein kinase, inside the cell. In a series of highly specific steps, during which one kinase after another becomes phosphorylated and activated, the signal is transduced until some specific kinase is activated that has broadspread effects. Mitogen Activated Protein Kinase (MAP-kinase) lies at the end point of one of these phosphorylation cascades. After being activated, MAP-kinase has a large number of targets which lead to broad changes in the cell's metabolism. The particular kinase that lies immediately upstream of MAP-kinase in this cascade and activates MAP-kinase is called MAP-kinase-kinase, MAPKK or specifically in our case MEK (MAP kinase/Erk kinase).

Clones of MAP-kinase (erk-2) and its corresponding activator MEK-2 have been prepared by others (Her, et al., *Nucleic Acids Res.*, 19:3743 (1991); GenBank Accession No. X58712; Wu, et al., *Mol. Cell. Biol.*, 13:4539 (1993); GenBank Accession No. L14936, the disclosures of which are hereby incorporated by reference herein). However, these clones do not provide fully active kinases when expressed in *E. coli*, because both kinases need to be phosphorylated before they become active. It is known in a number of systems that instead of the normal route of phosphorylating a serine, threonine, or tyrosine residue by an upstream kinase, it is frequently possible to substitute the target residue by an acidic residue such as aspartic acid or glutamic acid to obtain a functional kinase (Fabian, et al., *Mol. Cell. Biol.*, 13:7170 (1993), the disclosure of which is hereby incorporated by reference herein). What's important is not so much the phosphorylation, as the charge that is produced at the appropriate position. Mutations have been reported, for example, in MEK-1 (a homolog of MEK-2) that lead to it being constitutively active (Mansour, et al., *Science*, 265:966 (1995), the disclosure of which is hereby incorporated by reference herein). Two of these mutations S218D and S222D, involve serine to aspartic acid changes. Other mutants contain an additional modification of a 20 amino acid deletion close to the N-terminus in combination with the acidic residue substitutions. These mutants were tested for their ability to transform mammalian cells. See, e.g., Mansour, et al., supra (1995).

In general, there is a considerable advantage to producing eukaryotic protein kinases in *E. coli* because *E. coli* does not normally carry protein kinases, whereas a typical eukaryotic cell may make many hundreds of protein kinases. Thus, the purification of protein kinases from eukaryotic cells can be quite difficult because many of the protein kinases have similar properties and co-purify. These contaminating kinases are often impossible to assay because their specific substrates are not known. Thus, if the kinase is produced from a native source one cannot with any absolute certainty be sure that it does not contain trace amounts of a contaminating kinase. When a researcher is then using that kinase and discovers that it has a low level of activity against a protein that they are working with, they are left with a potential dilemma of not knowing whether it is just that their protein is a poor substrate for the real protein kinase, which is the major component in the preparation. By producing protein kinases directly from *E. coli* these difficulties can be overcome.

Accordingly, there is a continuing need for the development of new methods for the cloning and expression of phosphorylation-dependent protein kinases in *E coli*.

SUMMARY OF THE INVENTION

The present invention relates to methods for the cloning and expression of phosphorylation-dependent protein kinases (hereinafter sometimes referred to as "PDPK"). More specifically, the present invention comprises a method for cloning and expressing an exogenous PDPK in *E. coli* which is normally inactive when expressed in *E. coli*, by: 1) isolating DNA which encodes an activating protein (e.g., one which activates the PDPK) and 2) co-expressing in *E. coli* the DNA encoding the PDPK with the DNA coding for the activating protein.

In certain preferred embodiments, the activating protein and PDPK are components of a signal transduction pathway such as the MAP or SEK pathways (Marshall, *Cell*, 80:179 (1995); Yan, et al., *Nature*, 372:798 (1994), the disclosures of which are hereby incorporated by reference herein) pathways. Other pathways include the PI(3)K-mediated signaling pathway (Burgering, et al., *Nature*, 376:599 (1995), the disclosure of which is hereby incorporated by reference herein).

In other preferred embodiments, either or both of the activating peptide or PDPK may be expressed as a fusion protein with a fusion partner to facilitate, for example, purification of the target PDPK. This would be particularly desirable in practicing the instant invention where the activating protein is an upstream kinase. In this case, the *E. coli* strain would contain two kinases which could give rise to the complication that the target PDPK is contaminated with its upstream kinase. However, the presence of a fusion system would be of a considerable advantage in either removing the upstream kinase (assuming that it is the upstream kinase which is fused) and/or in the direct purification of the PDPK, or both.

As used herein "phosphorylation-dependent protein kinase" or "PDPK" means a protein kinase that must itself be phosphorylated before it is able to catalyze the phosphorylation of its substrate proteins.

As used herein "activating protein kinase" means a protein kinase or portion thereof that specifically phosphorylates a target protein, thereby inducing the target protein to function as a protein kinase.

As used herein "signal-transduction pathway" means a network of proteins that transduces a signal from one part of a cell to another. The transduction is usually mediated by chemical modifications of each intermediate protein catalyzed by its immediate upstream protein in the pathway.

As used herein "upstream component" means a protein that lies in a signal transduction pathway and which is not the final target of the pathway.

As used herein "fusion protein" means a protein that contains at least two domains, one of which is a specific sequence of amino acids chosen to facilitate purification, the other domain being the catalytically active portion of the protein.

DETAILED DESCRIPTION OF THE INVENTION

Figure 1:
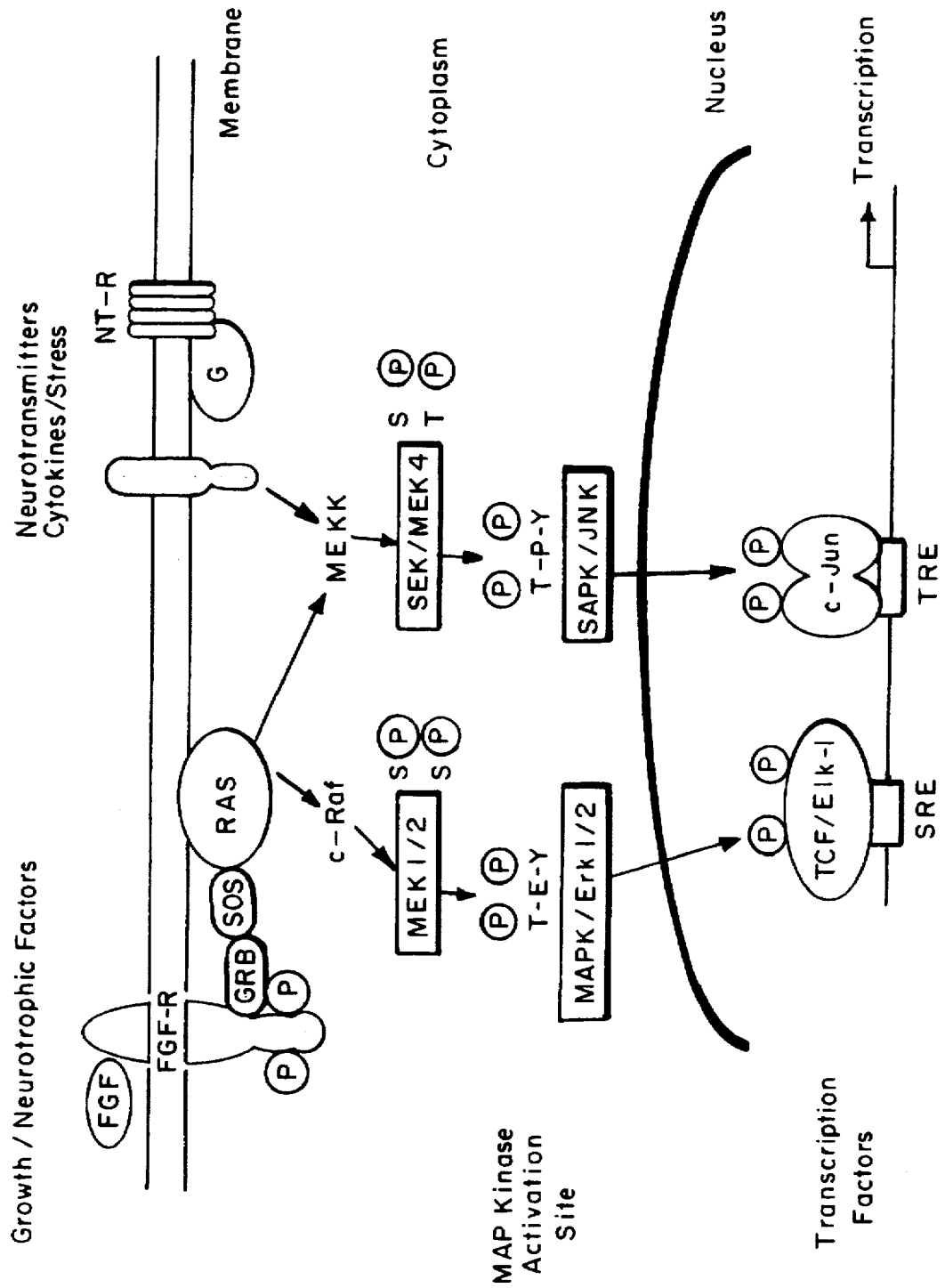
FIG. 1 depicts growth factor and stress-activated signal-transduction pathways.

In accordance with the present invention, there is provided a method for reproducing individual or whole parts of phosphorylation cascades (or signal transduction pathways) in E. coli such that downstream portions of the cascade are produced in fully active form.

A general scheme for expressing a phosphorylation dependent protein kinase in E. coli would require: 1) a clone of the PDPK gene inserted into a suitable vector for expression in E. coli, and 2) a clone of the gene for the activating kinase also inserted into a suitable vector for expression in E. coli. The latter gene might need to be engineered so that it contained an activating mutation such that when expressed in E. coli it would be functional.

Many activating protein kinases are already known and their genes have been cloned (Hardie and Hanks (eds.), The Protein Kinase Facts Books, "Protein-tyrosine kinases" page 246 and "Protein-serine kinases" page 418, Academic Press (1995), the disclosure of which is hereby incorporated by reference herein). In some cases, activating mutations have been described (Huang and Erikson, Proc. Natl. Acad. Sci., U.S.A., 91:8960–8963 (1994); Brunet, et al., EMBO J., 13:3003–3010 (1994), the disclosures of which are hereby incorporated by reference herein). Typically, an activating mutation is one that replaces a serine, threonine or tyrosine residue that is the target for phosphorylation, by an acidic residue such as aspartic acid or glutamic acid (Huang and Erikson, supra (1994) and Brunet, et al., supra, (1994)).

Such replacement could be carried out by site-directed mutagenesis (Kunkel, et al., Meth. Enzymology, 154:367–382 (1987); Solomon, et al., Mol. Biol. Cell., 3:13–127 (1992); Fresquet, et al., EMBO J., 12:3111–3121 (1993); Poon, et al., EMBO J., 12:3123–3132 (1993); Solomon, et al., EMBO J., 12:3133–3142 (1993), the disclosures of which are hereby incorporated by reference herein). Where the activating protein kinase is unknown, then it would need to be identified by, for example, using the unphosphorylated PDPK as a substrate in a typical phosphorylation assay to isolate, purify and characterize it (Hunter and Sefton (eds), Protein Phosphorylation Part A, page 763 and Part B, page 547, Methods in Enzymology, volumes 200 and 201, Academic Press, (1991), the disclosure of which is hereby incorporated by reference herein). The assay would consist of taking the substrate PDPK in its unphosphorylated, inactive state and treating it with a cell extract containing an activating kinase. If an activating phosphorylation took place, then the PDPK would become active and could itself phosphorylate a suitable substrate included in the reaction mixture. As a control, the activating kinase would be incubated with the test substrate in the absence of PDPK and no phosphorylation would take place.

Once the activating protein kinase has been purified to homogeneity, then in general, segments of its amino acid sequence would be determined and DNA sequence probes could be made that would allow the isolation of the gene either using standard PCR protocols or by colony hybridization to appropriate cDNA libraries employing techniques commonly practiced (Sambrook, et al., Molecular Cloning: A Laboratory Manual, 2nd edition, Cold Spring Harbor Press (1989), the disclosure of which is hereby incorporated by reference herein). The gene would then need to be cloned and expressed in E. coli. If it was inactive in its native form as expressed in E. coli, presumably because it was itself a PDPK, then it could be activated by site-specific mutation as described above in order to replace key phosphorylation sites with acidic residues as indicated above. Alternatively, the further upstream activating kinase could itself be identified as above and cloned into E. coli. In this way a cascade of protein kinases, present in the original eukaryotic cell and necessary for activation of the final target PDPK, could be reconstructed in E. coli. In some cases, such as the cyclin-dependent protein kinases, several subunits might need to be present for activity (Solomon and Kirschner, Mol. Biol. Cell., 3:13–127 (1992); Fresquet, et al., EMBO J., 12:3111–3121 (1993); Poon, et al., EMBO J., 12:3123–3132 (1993); Solomon, et al., EMBO J, 12:3133–3142 (1993), the disclosures of which are herein incorporated by reference herein)). In this case, it might be necessary to include several steps in the phosphorylation cascade, each cloned into a single strain of E. coli and thereby reconstituting a part of the cascade, before a suitable upstream activating kinase could be obtained in fully functional form.

In accordance with another embodiment of the invention, the activating protein kinase, once cloned could be prepared as a fusion protein capable of purification in a single step by affinity chromatography (EPO Publication No. 0 286 239, the disclosure of which is hereby incorporated by reference herein). One preferred fusion partner is maltose-binding protein ("MBP") (Riggs, "Expression and purification of maltose-binding protein fusions". In Current Protocols in Molecular Biology (Ausubel, et al., eds.), Greene Publishing and Wiley-Interscience, New York (1992), the disclosure of which is hereby incorporated by reference herein). Other suitable binding elements include S-streptavidin (Novagen Technical Literature based on Potts, et al., J. Biol. Chem., 238:2593–2594 (1963), the disclosure of which is hereby incorporated by reference herein). STREP-TAG (Schmidt and Skerra, *Protein Engineering*, 6:109–122 (1993), the disclosure of which is hereby incorporated by reference herein) and His-tag (Hochuli, et al., *J. Biol. Chem.*, 263:7211–7215 (1988), the disclosure of which is hereby incorporated by reference herein). These fusion partners also facilitate either purification of the PDPK to homogeneity or removal of the activating protein kinase during the purification of the final PDPK. This could be accomplished by standard recombinant DNA procedures (Sambrook, et al., supra (1989), the disclosure of which is hereby incorporated by reference herein).

Typically, the activating protein kinase constructed as a fusion protein would be co-expressed with the PDPK from the same plasmid construct and would be under the control of the same promoter or a separate promoter depending on the level of expression needed. Preferably, the promoter would be an inducible one such as ptac (ptac), lambda $P_L$ (lambda $P_L$) or T7 (promoter T7). Expression of the activating protein kinase could be much less than that of the PDPK, since its activity is needed only in catalytic amounts. Its limited expression would facilitate its removal during purification of the PDPK. Differential expression of the activating kinase and PDPK could be achieved using different promoters. For example, the expression of the activating kinase could be temperature regulated using the lambda $P_L$ promoter while PDPK expression could be IPTG induced using the ptac promoter.

In some circumstances, it may be desirable to express the activating kinase from the chromosome of *E. coli*, in which case its gene would be transferred into a phage DNA, such as bacteriophage lambda, and *E. coli* would be lysogenized with the construct (Sambrook, et al., supra (1989); Bao, et al., *Gene*, 109:167–168 (1991); Luckow, et al., *J. Virol.*, 67:4566–4579 (1993); Winans, et al., *J. Bacteriol.*, 161:1219–1221 (1985); Russell, et al., *J. Bacteriol.*, 171:2609–2613 (1989), the disclosures of which are hereby incorporated by reference herein). By using an inducible promoter, such as one of the early promoters of phage lambda (lambda $P_L$) or the lac promoter, the expression of the activating kinase could be easily controlled so as to maximize its expression in conjunction with the expression of the PDPK.

Once the desired strains containing both the target PDPK and its upstream activating kinase(s), expressed as a fusion protein(s), have been constructed, then production of the PDPK would involve growing the strain, inducing expression of the PDPK (e.g., with IPTG if the kinase gene is under the control of the lac promoter) and its activating kinase(s) and preparing cell extracts. Purification involves removing cell debris by centrifugation and then passing the extract over a suitable affinity column, such as amylose resin for MBP fusions (Ferenci and Klotz, *FEBS Letters*, 94:213–217 (1978), the disclosure of which is hereby incorporated by reference herein), to remove any contaminating activating kinase. Fractionation of the remaining proteins may be accomplished by standard column chromatography over appropriate columns to give the desired PDPK as a homogenous protein. (See, for example, Hunter and Sefton, *Methods in Enzymology*, 200:763 (1991) and Hunter and Sefton, *Methods in Enzymology*, 201:547 (1991), the disclosures of which are hereby incorporated by reference herein.)

The following Examples are given to illustrate embodiments of the present invention as it is presently preferred to practice. It will be understood that these Examples are illustrative, and that the invention is not to be considered as restricted thereto except as indicated in the appended claims.

EXAMPLE I

Materials and Methods

A clone of MAP-kinase (pET3aMAPK), its corresponding activator MEK2 (pBSSKMEK2 222/226D T404A) and unphosphorylated MAPK protein were obtained from Dr. M. Weber at the University of Virginia. Molecular biology reagents such as restriction enzymes, oligonucleotide primers and amylose resin were provided by New England Biolabs, Inc. (Beverly, Mass.). Protein purification resins were purchased from Pharmacia (Piscataway, N.J.). Phosphocellulose units were obtained from Pierce (Rockford, Ill.). ECL western blotting system and antibodies were purchased from Amersham (Arlington Heights, Ill.). Myelin basic protein (MyBP) and phosphocellulose disks were purchased from Gibco/BRL (Gaithersburg, Md.). Phospho-specific MAPK antibody was supplied by New England Biolabs, Inc. (Beverly, Mass.). Molecular biology techniques used were standard protocols, see Maniatis, et al., *Molecular Cloning: A Laboratory Manual* (1989), Volume 2, 2nd Edition (the disclosure of which is hereby incorporated by reference herein). Standard techniques to study kinase activity were described in Hardie, et al., *Protein Phosphorylation A Practical Approach* (1993), the disclosure of which is hereby incorporated by reference herein.

Mutation Of MEK2 To Allow For Constitutive Activation

Figure 2:
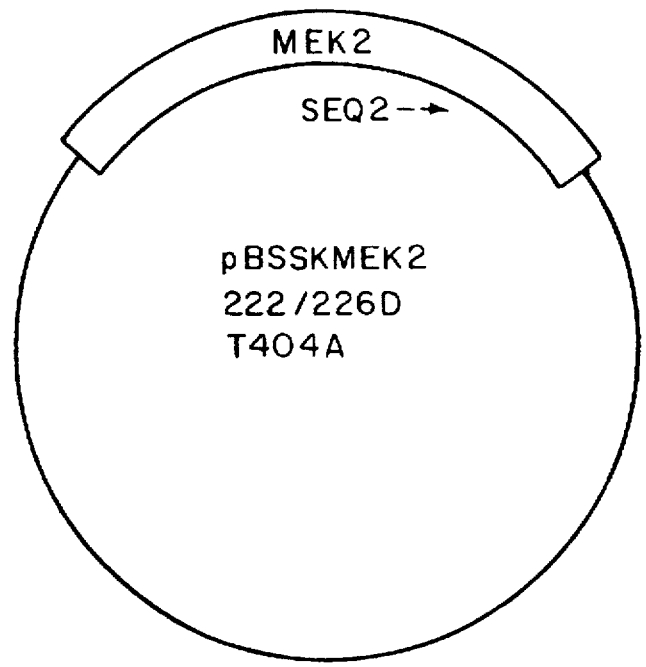
FIG. 2 outlines the strategy employed to generate the N-terminal deletion mutant of MEK2.
Figure 2:
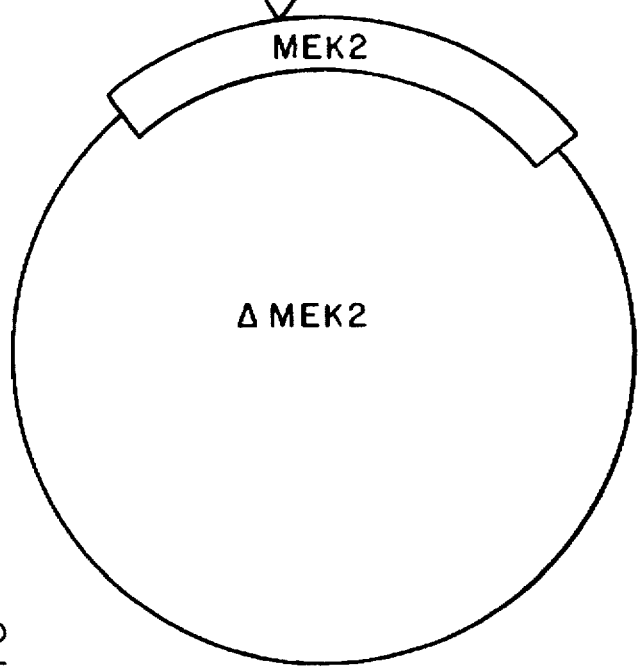

Mutations have been reported in MEK1 (a homolog of MEK2) that confer constitutive activity (Mansour, et al., *Science*, 265:966 (1995); Huang, et al., *Proc. Natl. Acad. Sci. U.S.A.*, 91:8960 (1994), the disclosures of which are hereby incorporated by reference herein). Two of these mutations, at positions S218 and S222 of MEK1, involve substituting the serines with an acidic residue such as aspartic acid or glutamic acid to obtain a functional kinase. Introducing a negatively charged residue may mimic the effect of phosphorylation at these sites. Aspartic acid residues at the corresponding sites in MEK2 (GenBank Accession No. L14936) were introduced by site-directed mutagenesis (Dr. M. Weber, University of Virginia). This clone (pBSSKMEK2 222/226D T404A) was further modified by introducing a 24 amino acid residue deletion close to the N-terminus. This deletion was created as shown in FIG. 2 by inverse PCR reaction using as primers:

StuI
5'CACCAGGTAGGCCTCGGAGGCGCCCTCG3'   (SEQ ID NO:1)

and

5'AAGCCGGCTGGAGGCCTTCCTTACCCAG3'   (SEQ ID NO:2)

The PCR reaction was set up adding in the following order: 50 µl 10X Vent Buffer (100 mM KCl, 200 mM Tris-HCl (pH 8.8) 100 mM $(NH_4)_2$ $SO_4$), 20 mM $MgSO_4$, 1% Triton X-100), 323 µl $H_2O$, 10 µl 100 mM $MgSO_4$, 20 µl 25 mM dNTPs, 5 µl BSA 2 µl pBSMEK2 DNA (0.1 µg/µl), 40 µl of each primer (10 µM), 10 units Vent DNA Polymerase. The reaction mix was aliquoted (50 µl) into 10 tubes. The segments of each PCR cycle (20 total) were the following: 1 min. at 95° C., 1 min. at 32° C. and 1 min. at 72° C. The 10 reactions were pooled and subjected to agarose (low melting point) gel electrophoresis with ethidium bromide present to visualize the DNA products. A DNA band of approximately 4,300 base pairs was excised from the gel and purified using β-agarase I. After ethanol precipitation, the DNA pellet was resuspended in 50 µl TE Buffer (20 mM Tris-HCl (pH 7.5), 1 mM EDTA) and digested with the restriction enzyme StuI. The reaction was subjected to agarose (low melting point) electrophoresis. A DNA band of approximately 4,300 bp was excised from the gel and melted at 65° C. To 15 µl of molten gel was added 2 µl 10X Ligase Buffer (500 mM Tris-HCl (pH 7.8), 100 mM MgCl₂, 100 mM dithiothreitol, 10 mM ATP, 250 µg/ml BSA) and 40 units concentrated ligase. The ligation was incubated at 16° C. overnight. The ligation was transformed into New England Biolabs' (Beverly, Mass.) *E. coli* strain ER2417. Mini-plasmid preparations of transformants were analyzed by restriction digestion; two clones (ΔMEK2) were identified to contain the 72 base pair deletion which was confirmed by DNA sequence analysis.

Overexpression of MEK

A. Construction Of A Vector To Express MBP-ΔMEK Protein

The MEK was expressed as a protein fusion with maltose binding protein (MBP) by generating a DNA fragment by PCR of the deletion mutant ΔMEK2 using the following primers:

```
             NheI
5'AGAGCCCTGATGCTAGCCCGGAGG3'     (SEQ ID NO:3)

and

EcoRI
5'TTGCGAATTCTGTTACACTGCAGTACG3'  (SEQ ID NO:4)
```

The PCR reaction was set up adding in the following order: 50 µl 10X Vent Buffer (100 mM KCl, 200 mM Tris-HCl (pH 8.8) 100 mM (NH₄)₂ SO₄, 20 mM MgSO₄, 1% Triton X-100), 378 µl H₂O, 25 µl 100 mM MgSO₄, 20 µl 25 mM dNTPs, 5 µl BSA, 2 µl ΔMEK2 clone 3 DNA (0.1 µg/µl), 5 µl of each primer (1 mM), 10 units Vent DNA Polymerase. The reaction mix was aliquoted (50 µl) into 10 tubes. The segments of each PCR cycle (25 total) were the following: 1 min. at 95° C., 1 min. at 32° C., and 1 min. at 72° C. The 10 reactions were pooled and subjected to agarose (low melting point) gel electrophoresis with ethidium bromide present to visualize the DNA products. A DNA band of approximately 1,300 base pair was excised from the gel and purified using β-agarase I. After digesting the fragment with NheI, the overhangs were blunt ended using Klenow DNA polymerase under standard reaction conditions. The fragment was digested with EcoRI to allow for ligation into the pMAL-c2 vector which was previously digested with XmnI and EcoRI. The ligation was performed at 16° C. overnight. The ligation was transformed into New England Biolabs' (Beverly, Mass.) *E. coli* strain ER2147. Mini-plasmid preparations of transformants were analyzed by restriction digestion and clones pMALc2ΔMEK2.8, 2.17, and 2.28 were identified to have the correct insert.

B. Protein Purification of MBP-ΔMEK Fusion

A 1 liter culture of *E. coli* strain TB1 carrying pMALc2ΔMEK2.8 was grown in media containing 10 g/liter tryptone, 5 g/liter yeast extract, 5 g/liter NaCl and 100 mg/liter ampicillin at 37° C. At mid-exponential growth phase, 1 mM IPTG was added and the culture was incubated at 37° C. for an additional 4 hours. The cells were harvested by centrifugation. The cell pellet was suspended in STE Buffer (150 mM NaCl, 50 mM Tris-HCl (pH 7.2), 1 mM EDTA) containing a protease inhibitor cocktail of 2 mM PMSF, 10 µg/ml aprotinin, 10 µg/ml pepstatin, 10 µg/ml leupeptin and 10 mM benzamidine. The cells were lysed by sonication. The crude extract was clarified by centrifugation before batch purification at 4° C. for 30 min. using 1 ml of amylose resin previously washed with 10 ml STE buffer with 2 mM PMSF. The resin was washed 3 times with 10 ml STE buffer with 2 mM PMSF. MEK activity was assayed using two methods as described below.

C. MEK Activity

MEK activity as an MBP fusion protein was assayed indirectly for its ability to phosphorylate and activate MAPK. After phosphorylation by MEK, the modified MAPK was tested for its ability to phosphorylate an exogenous substrate, myelin basic protein. It was also examined by western blot analysis for phosphorylation on its critical tyrosine (Y185) which is required for enzyme activity. A 1 ml reaction was set up to modify MAPK as follows: 0.5 ml MBPMEK2 amylose beads (as prepared above) was suspended in 0.1 ml 10X cdc2 Buffer (500 mM Tris-HCl (pH 7.5), 100 mM MgCl₂, 10 mM dithiothreitol, 10 mM EGTA), 20 µl 0.1M ATP, 0.4 ml H₂O and 25 µg purified unphosphorylated MAPK. The reaction was incubated at 30° C. and at time 0, 15, 30, 45, 60, 90 and 120 min., 50 µl of the reaction was removed for western blot analysis and 20 µl was removed to measure MAPK activity.

D. Western Blot Analysis

The 50 µl samples were centrifuged to separate the MBPΔMEK2 amylose beads from the MAPK protein. The supernatant (20 µl) was loaded onto a SDS-PAGE gel (10–20% gradient), electrophoresed, and blotted onto a nitrocellulose membrane. A standard western blot was performed using a phosphospecific rabbit polyclonal antibody that preferentially recognized MAPK when it is phosphorylated on Y185 (New England Biolabs, Inc., Beverly, Mass.). The membrane was developed using the ECL western blot system (Amersham, Arlington Heights, Ill.).

Figure 3:
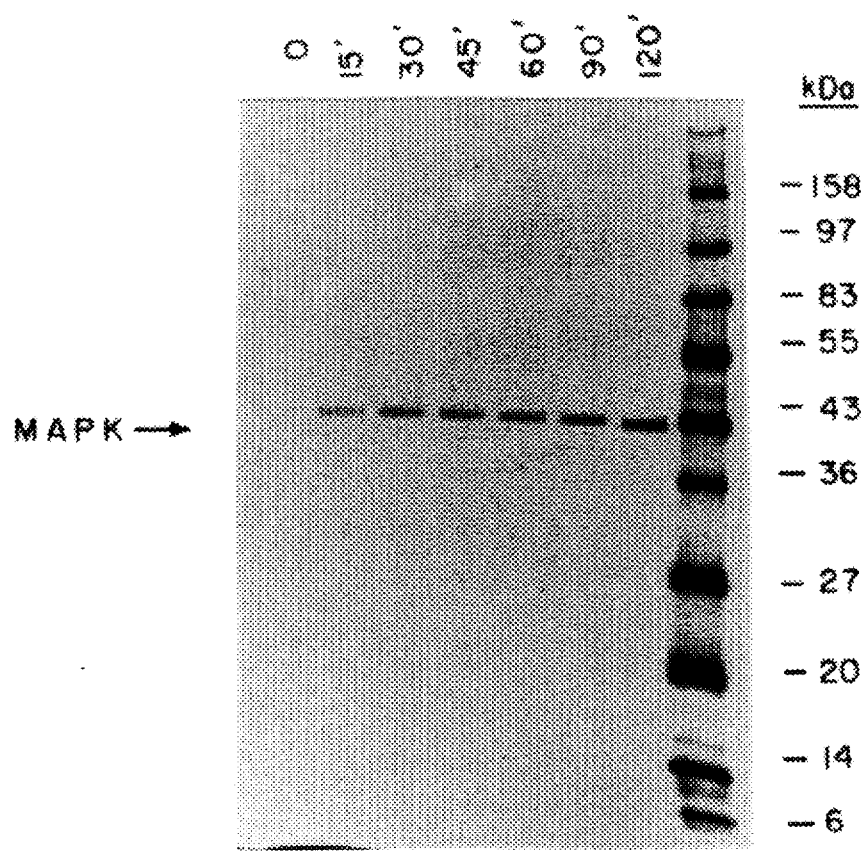
FIG. 3 is a western blot demonstrating the gradual increase in phosphorylation of MAPK (at tyrosine 185) after activation by MBPΔMEK2 in vitro over time (min).

FIG. 3 is an autoradiogram of the western blot demonstrating the gradual increase in phosphorylation of MAPK (at tyrosine 185) after activation by MBPΔMEK2 in vitro over time (min).

E. MAPK Activity

Figure 4:
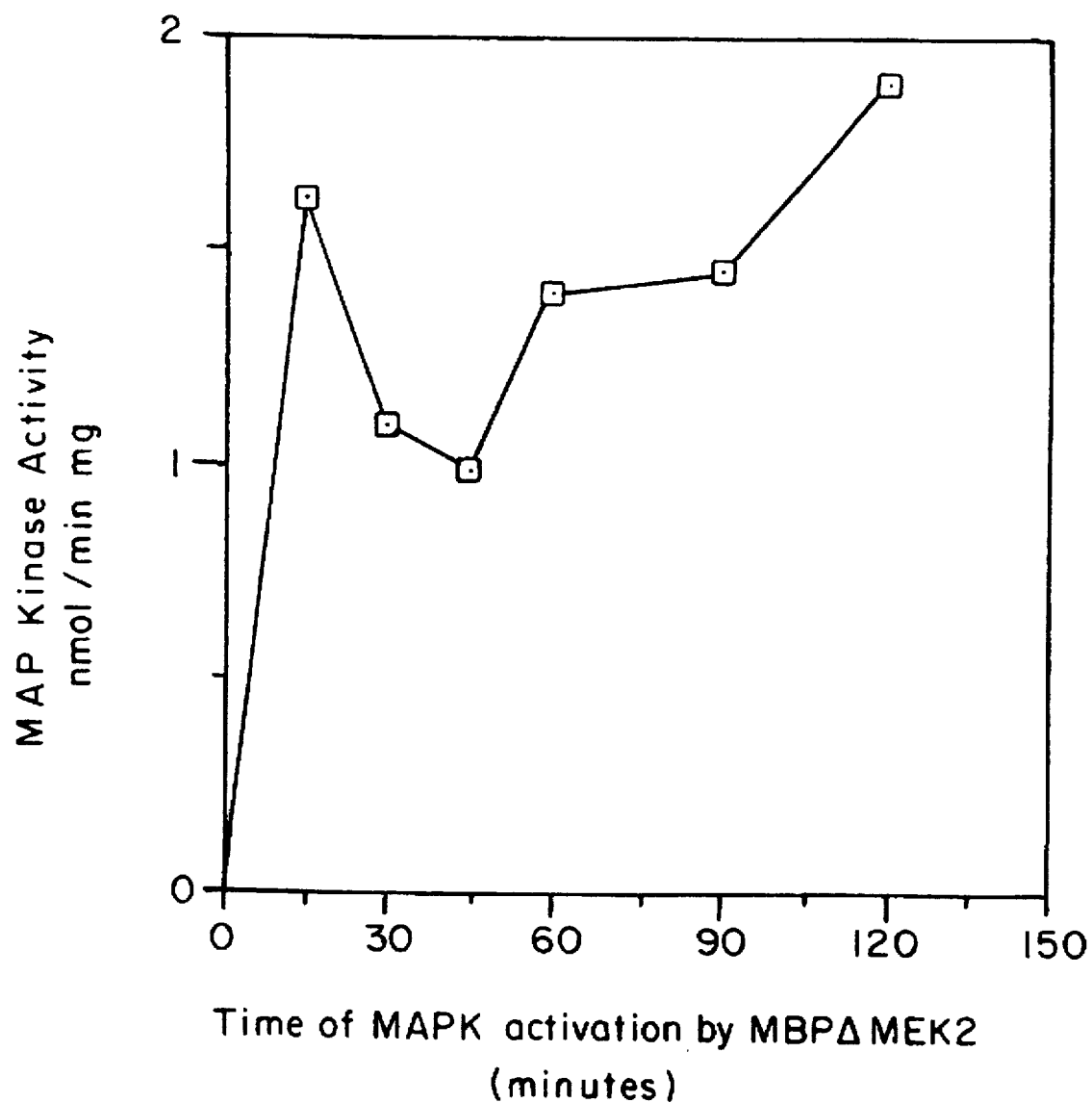
FIG. 4 plots the activation of MAPK by MBPΔMEK2 in vitro over time (min) as measured indirectly by the ability of MAPK to phosphorylate myelin basic protein.

The 20 µl samples were centrifuged to separate the MBPΔMEK2 amylose beads from the MAPK protein. The supernatant (5 µl) was assayed for kinase activity under standard assay conditions. Briefly, the samples were added to a 10 µl reaction containing 10 µM myelin basic protein, 100 µM ATP, gamma-33P ATP (~1,800 cpm/pmol), in 1X cdc2 Buffer. After 10 min. at 30° C., the reaction was spotted onto a phosphocellulose disk. After washing with 75 mM phosphoric acid, the disks were analyzed in a scintillation counter. FIG. 4 plots the activation of MAPK by MBPΔMEK2 over time as measured indirectly by the ability of MAPK to phosphorylate myelin basic protein.

Co-Expression MEK And MAPK

A. Construction of pMALc2MEKT7MAPK (MM2+MM3)

The MAPK (GenBank Accession No. 58712) gene was cloned into the vector pET3a (Novagen, Madison, Wis.) which provides for inducible expression of unphosphorylated MAPK when in a host cell such as *E. coli* strain BL21 DE3 (Novagen, Madison, Wis.) that contains a source of T7 RNA polymerase. A DNA fragment (approximately 1,300 base pairs) generated by digestion of pET3aMAPK DNA (from Dr. M. Weber, University of Virginia) with SphI and EcoRV was initially subcloned into LITMUS38 (New England Biolabs, Inc., Beverly, Mass.) vector to create convenient restriction sites for ligation into pMALc2MBPΔMEK2. A DNA fragment (approximately 1,300 base pairs) generated by digestion of LITMUS38MAPK with HindIII and SalI was subcloned into pMALc2MBPΔMEK2. The ligations were transformed into

Figure 5:
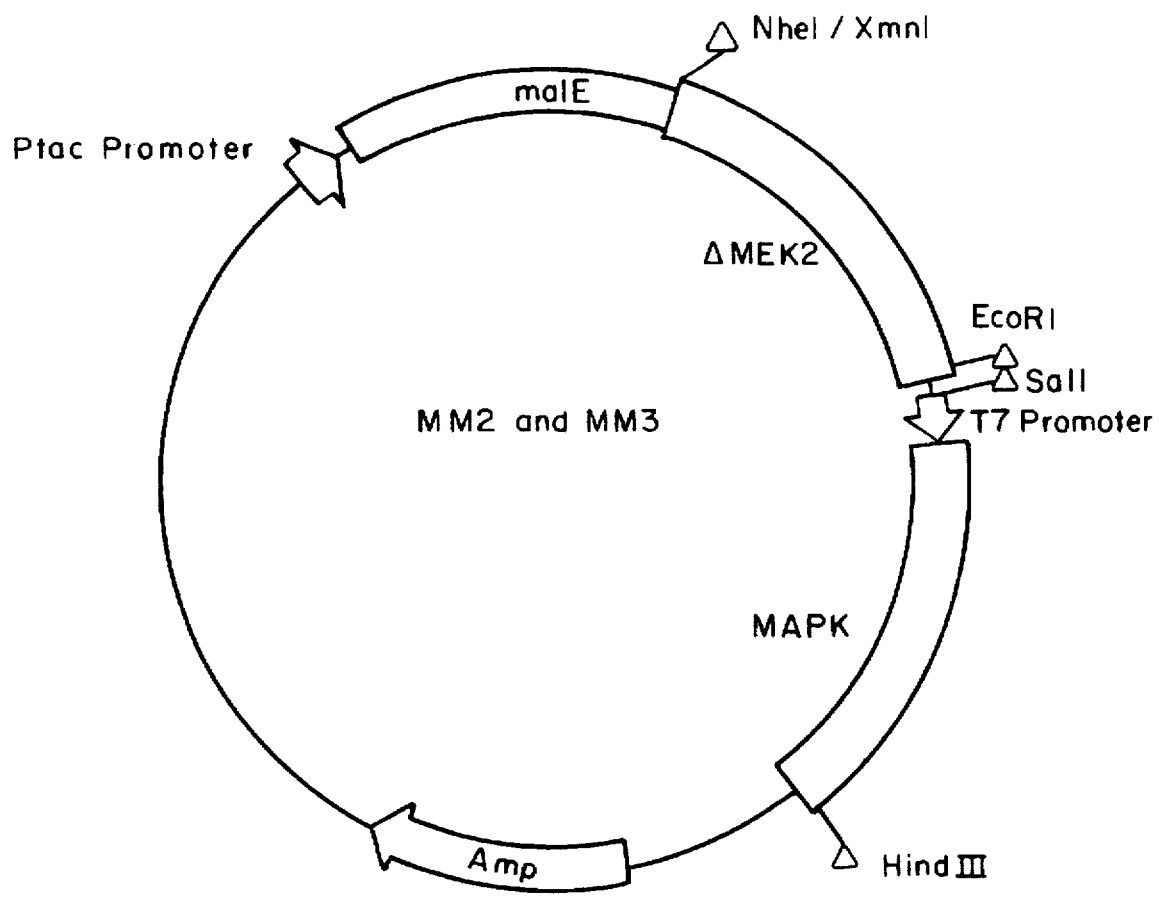
FIG. 5 is a plasmid map of clones MM2 and MM3 which provide for expression of both MBPΔMEK2 and MAPK in E. coli strain BL21 DE3.

*E. coli* strain BL21 DE3. Mini-plasmid preps of transformants were analyzed by restriction digestion and several clones of pMALc2ΔMEKT7MAPK were identified to have the correct insert. Two clones designated MM2 and MM3 were analyzed for in vivo activation of MAPK. A plasmid map of the clones is shown in FIG. 5.

B. MAPK Activity

Figure 6:
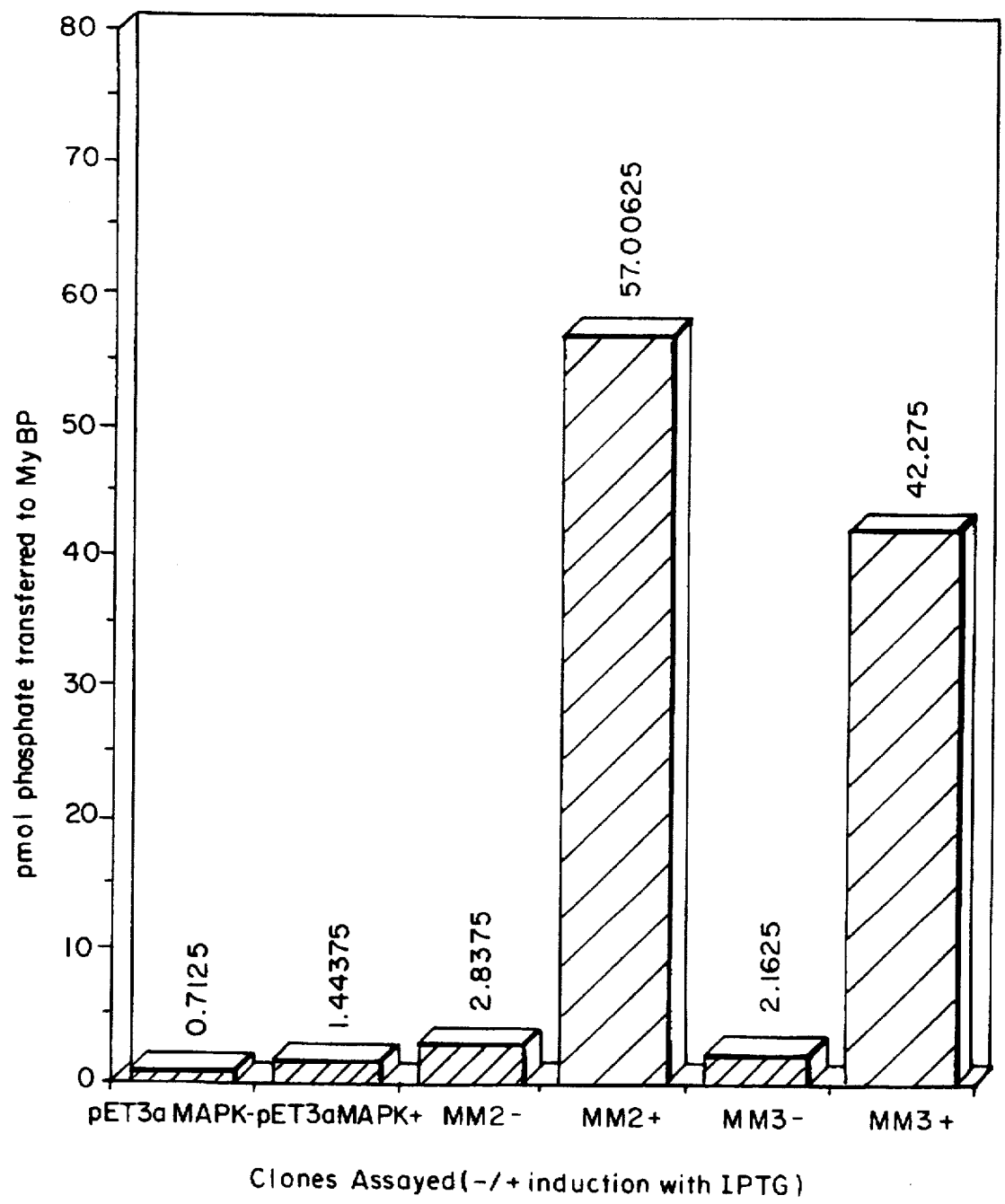
FIG. 6 demonstrates the ability of MBPΔMEK2 to activate MAPK in vivo by measuring MAPK activity in the crude extracts of clones MM2 and MM3±induction with IPTG.

Ten ml cultures (in duplicate) of *E. coli* strain BL21 DE3 carrying either clones MM2, MM3 or pET3aMAPK were grown in media containing 10 g/liter tryptone, 5 g/liter yeast extract, 5 g/liter NaCl and 100 mg/liter ampicillin at 37° C. At mid-exponential growth phase, one culture of each pair was induced with 1 mM IPTG. The cultures were incubated at 37° C. for an additional 4 hours. The cells were harvested by centrifugation. The cell pellet was suspended in Buffer A (25 mM Tris-HCl (pH 7.5), 25 mM NaCl, 2.5 mM EGTA, 2 mM EDTA and 1 mM DTT) containing a protease inhibitor cocktail of 2 mM PMSF, 10 μg/ml aprotinin, 10 μg/ml pepstatin, 10 μg/ml leupeptin and 10 mM benzamidine and a phosphatase inhibitor cocktail of 10 mg/ml p-nitrophenolphosphate, 1 mM sodium vanadate and 5 mM sodium fluoride. The cells were lysed by sonication. The crude extract was clarified by centrifugation before being assayed for enzyme activity using standard assay conditions. Briefly, 5 μl of the supernatant was added to a 30 μl reaction containing 10 μM myelin basic protein, 100 μM ATP, gamma-33P ATP (~500 cpm/pmol), in 1X cdc2 Buffer. After 10 min. at 30° C., the reaction was terminated by the addition of 5 μl of 0.5M EDTA. The reactions (25 μl) were spotted onto phosphocellulose units. The filter units were washed 2 times each with 0.5 ml of 75 mM phosphoric acid before analysis in a scintillation counter. The results are shown in FIG. 6. Very little, if any, kinase activity is detected in cell extracts prepared from the *E. coli* strain expressing only MAPK (pET3aMAPK±IPTG). The cell extracts from clones MM2 and MM3 which express both activated MEK and MAPK (+IPTG) demonstrate approximately a 20-fold increase in MAP activity over basal levels (−IPTG).

C. Purification

A 1 liter culture of *E. coli* strain BL21 DE3 carrying clone MM2 was grown in media containing 10 g/liter tryptone, 5 g/liter yeast extract, 5 g/liter NaCl and 100 mg/liter ampicillin at 37° C. At mid-exponential growth phase, 1 mM IPTG was added and the culture was incubated at 37° C. for an additional 4 hours. The cells were harvested by centrifugation. The cell pellet was suspended in Buffer A (25 mM Tris-HCl (pH 7.5), 25 mM NaCl, 2.5 mM EGTA, 2 mM EDTA and 1 mM DTT) containing a protease inhibitor cocktail of 2 mM PMSF, 10 μg/ml aprotinin, 10 μg/ml pepstatin, 10 μg/ml leupeptin and 10 mM benzamidine and a phosphatase inhibitor cocktail of 10 mg/ml p-nitrophenolphosphate, 1 mM sodium vanadate and 5 mM sodium fluoride. The cells were lysed by sonication. The crude extract was clarified by centrifugation before batch purification at 4° C. for 30 min. using 5 ml of amylose resin previously washed with 50 ml Buffer A with 2 mM PMSF. The supernatant was applied to a column of phenyl sepharose (2.6×15 cm) equilibrated with Buffer B (25 mM Tris-HCl (pH 7.5), 25 mM NaCl, 2.5 mM EGTA, 2 mM EDTA, 1 mM DTT and 9% ethylene glycol). The column was washed with 50 ml of Buffer A followed by increasing linear gradient of ethylene glycol (9–60%) in 150 ml of Buffer A (flow rate, 2 ml/min.; 5 ml fractions). MAPK eluted between 50–60% ethylene glycol and pooled fractions were diluted with 100 ml Buffer A before being loaded onto a column of Q-sepharose (1.0×10 cm) equilibrated with Buffer A. The column was washed with 20 ml of Buffer A followed by increasing linear gradient of NaCl (0.025–1M) in 150 ml Buffer A (flow rate 1 ml/min.; 2 ml fractions). The enzyme eluted between 0.4–0.55M NaCl and pooled fractions were diluted with 4 ml of Buffer B with 60% ethylene glycol to a final concentration of 15% ethylene glycol before being applied to a Phenyl Superose HR 10/10 (8 ml) column equilibrated with Buffer B. The column was washed with 15 ml of Buffer B followed by a linear increasing gradient of ethylene glycol (9–60%) in 150 ml of Buffer B (flow rate, 2 ml/min.; 1.5 ml fractions). The enzyme eluted between 30–40% ethylene glycol and the pooled fractions were stored at −80° C. A yield of 50,000 units of >90% pure MAPK as shown by SDS-PAGE was obtained.

EXAMPLE II

This method for cloning and expressing an exogenous phosphorylation-dependent protein kinases (PDPK) in *E. coli* could be applied to components, for example, of other signal transduction pathways (FIG. 1) such as those involved in the stress activated (Yan, et al., supra (1995)) or PI(3)-mediated (Burgering, et al., supra (1995)) signaling pathways. Proteins of such pathways which are not normally phosphorylated when expressed in *E. coli*, could be produced in a fully phosphorylated active form when co-expressed with the protein kinase responsible for its activation. For example, there is evidence that phosphorylation of two sites on the stress-activated protein kinase (SAPK) by the protein kinase SEK are necessary for full enzymatic activity (Kyriakis, et al., *Nature*, 369:156 (1994), the disclosure of which is hereby incorporated by reference herein). Similarly, it appears that SEK requires phosphorylation at two sites for full enzymatic activity (Yan, et al., supra (1995)). Using standard molecular biology techniques (Sambrook, et al., supra (1989)), one could replace the key phosphorylation sites of SEK with acidic residues such as glutamic or aspartic acid in an attempt to obtain a functional kinase which then could be used to activate SAPK. If SEK was cloned in a plasmid vector such as LITMUS38 (New England Biolabs, Inc., Beverly, Mass.), one could use inverse PCR to introduce the nucleotide changes by using the following primers:

```
     NruI     Asp
5'TTTTTCGCGAAGGAAAGAGATGCTGGG3'   (forward)
```

(SEQ ID NO:5)

and

```
5'TTTTTCGCGATATCGTCCACAAGCTGTCCACT3'   (reverse)
        GAT (reverse)
        Asp
```

(SEQ ID NO:6)

After digesting with the restriction enzyme NruI, the PCR product could be subjected to agarose (low melting point) gel electrophoresis for purification of a DNA band of approximately 4,000 base pairs. This band could be excised from the gel, purified using β-agarase I and subsequently ligated to form a plasmid vector carrying the mutated SEK.

After confirming the presence of the mutation by DNA sequence analysis, the mutated SEK could be expressed, possibly as a fusion protein with maltose binding protein (MBP) or other suitable tags. SEK could be subcloned into the vector pMAL-c2 for expression as an MBP fusion protein by first generating a DNA fragment by PCR of the mutated SEK using the following primers:

FspI
5'TTTT<u>TGCGCA</u>GCTCCGAGCCCGAGC3'    (SEQ ID NO:7)

5'TTTT<u>GGATCC</u>GTATCAGTCGACATACAT3'    (SEQ ID NO:8)
     BamHI

The PCR product could be gel purified as described above before digestion with FspI and BamHI. Digestion of the PCR product using these two restriction enzymes would allow for ligation into the pMAL-c2 vector (previously digested with XmnI and BamHI).

After identification of clones with the correct insert (DNA restriction analysis), the SEK fusion protein could be prepared and tested for kinase activity. Since SEK would be expressed as a MBP fusion protein, it could be easily purified using amylose beads. Once bound to the beads, SEK could be tested for enzymatic activity directly by performing a standard kinase assay using SAPK as a substrate. The alternative would be to assay its activity indirectly by activating SAPK in vitro and testing SAPK's ability to phosphorylate an exogenous substrate such as c-jun (Yan, et al., supra (1994)). Once it has been confirmed that the SEK mutant is constitutively active, it could be used to activate SAPK in vivo by co-expressing it with SAPK on the same plasmid vector. This could be performed by first introducing SAPK into a pET vector such as pET3a (Novagen, Madison, Wis.) which provides for inducible expression of unphosphorylated SAPK when in a host cell such as *E. coli* strain BL21 (DE3) (Novagen, Madison, Wis.) that contains a source of T7 RNA polymerase. The entire T7 transcription/expression region carrying SAPK could be excised from the pET3a vector using SalI and EcoRV for subcloning into the pMAL-c2 vector expressing active SEK. After identification of clones with the correct insert by DNA sequence analysis, SEK's ability to activate SAPK in vivo could be tested as previously described (Yan, et al., supra (1994)) using a c-jun as a substrate.

---

What is claimed is:

1. A method for cloning and expressing an exogenous phosphorylation-dependent protein kinase in *E. coli* which is normally inactive when expressed in *E. coli* comprising the steps of:

(a) isolating DNA which encodes an activating protein kinase, which activating protein kinase activates a phosphorylation-dependent protein kinase; and (b) co-expressing in an *E. coli* strain the isolated DNA of step (a) with DNA coding for the phosphorylation-dependent protein kinase.

2. The method of claim 1, wherein the phosphorylation-dependent protein kinase is at least one component of a signal-transduction pathway.

3. The method of claim 2, wherein the activating protein kinase is an upstream component of a signal-transduction pathway.

4. The method of claim 2, wherein the phosphorylation-dependent protein kinase comprises a eukaryotic protein kinase.

5. The method of claim 4, wherein the eukaryotic protein kinase is selected from the group of serine, threonine, histidine and tyrosine protein kinases.

6. The method of claim 5, wherein the eukaryotic protein kinase is a mitogen-activated protein (MAP) kinase.

7. The method of claim 6, wherein the upstream component of the MAP-kinase signal-transduction pathway comprises MEK-2 kinase or derivatives thereof.

8. The method of claim 1, wherein the activating protein kinase comprises an upstream component of a signal transduction pathway.

9. The method of claim 1, wherein the activating protein kinase is expressed as a fusion protein.

10. The method of claim 9, wherein the fusion partner comprises a binding protein which binding protein can be purified in a single step by affinity chromatography.

11. The method of claim 10, wherein the fusion partner comprises maltose binding protein.

12. The method of claim 1, wherein the phosphorylation-dependent protein kinase is expressed as a fusion protein.

13. The method of claim 12, wherein the fusion partner comprises a binding protein which binding protein can be purified in a single step by affinity chromatography.

14. The method of claim 13, wherein the fusion partner comprises maltose binding protein.

15. The method of claim 1, wherein isolated DNA encoding the activating protein kinase is incorporated into the chromosomal DNA of E. coli.

16. The method of claim 1, wherein the isolated DNA encoding the phosphorylation-dependent enzyme is incorporated into the chromosomal DNA of E. coli.

17. A method for purifying a phosphorylation-dependent protein kinase in E. coli comprising the steps of:
(a) co-expressing in E. coli (i) isolated DNA which encodes an activating protein kinase, which activating protein kinase activates a phosphorylation-dependent protein kinase and which is expressed as a fusion protein, with (ii) isolated DNA which encodes the phosphorylation-dependent protein kinase;
(b) contacting the co-expression product of step (a) with a substrate which binds to the fusion protein; and
(c) recovering the purified phosphorylation-dependent protein kinase from step (b).

18. The method of claim 17, wherein the phosphorylation-dependent protein kinase is at least one component of a signal-transduction pathway.

19. The method of claim 18, wherein the activating protein kinase is an upstream component of the signal-transduction pathway.

20. The method of claim 17, wherein the phosphorylation-dependent protein kinase comprises a eukaryotic protein kinase.

21. The method of claim 20, wherein the eukaryotic protein kinase is selected from the group of serine, threonine, tyrosine and histidine protein kinases.

22. The method of claim 21, wherein the eukaryotic protein kinase comprises MAP-kinase.

23. The method of claim 22, wherein the upstream component of the MAP-kinase signal-transduction pathway comprises MEK-2 kinase or derivatives thereof.

24. The method of claim 17, wherein the activating protein kinase comprises an upstream component of a signal transduction pathway.

25. The method of claim 24, wherein the fusion protein comprises binding proteins which can be purified in a single step by affinity chromatography.

26. The method of claim 25, wherein the fusion protein comprises maltose binding protein.

27. The method of claim 17, wherein the phosphorylation-dependent protein kinase is expressed as a fusion protein.

28. The method of claim 27, wherein the fusion partner comprises a binding protein which binding protein can be purified in a single step of affinity chromatography.

29. The method of claim 28, wherein the fusion partner comprises maltose binding protein.

30. The method of claim 17, wherein isolated DNA encoding the activating protein is incorporated into the chromosomal DNA of E. coli.

31. The method of claim 17, wherein the isolated DNA encoding the phosphorylation-dependent enzyme is incorporated into the chromosomal DNA of E. coli.

* * * * *

UNITED STATES PATENT AND TRADEMARK OFFICE
CERTIFICATE OF CORRECTION

PATENT NO. : 5,763,244

DATED : June 9, 1998

INVENTOR(S) : Wong-Madden, et al.

It is certified that error appears in the above-identified patent and that said Letters Patent is hereby corrected as shown below:

Column 8, line 15, replace "MBPMEK2" with -- MBPΔMEK2

Column 9, line 38, replace "(-IPTG)" with --(IPTG)--

Signed and Sealed this

Twenty-sixth Day of January, 1999

Attest:

*Attesting Officer*      *Acting Commissioner of Patents and Trademarks*